(12) United States Patent
Tsiaras et al.

(10) Patent No.: US 12,270,062 B2
(45) Date of Patent: *Apr. 8, 2025

(54) ELECTRONICALLY CONTROLLED SWAY BAR DAMPING LINK

(71) Applicant: Fox Factory, Inc., Duluth, GA (US)

(72) Inventors: Philip Tsiaras, Dacula, GA (US); Rick Strickland, Scotts Valley, CA (US)

(73) Assignee: Fox Factory, Inc., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/601,780

(22) Filed: Mar. 11, 2024

(65) Prior Publication Data

US 2024/0375474 A1 Nov. 14, 2024

Related U.S. Application Data

(63) Continuation of application No. 17/232,612, filed on Apr. 16, 2021, now Pat. No. 11,926,189, which is a
(Continued)

(51) Int. Cl.
*B60G 21/055* (2006.01)
*B60G 17/016* (2006.01)
(Continued)

(52) U.S. Cl.
CPC .......... *C12P 17/12* (2013.01); *B60G 17/0162* (2013.01); *B60G 17/0195* (2013.01);
(Continued)

(58) Field of Classification Search
CPC ............ B60G 21/0553; B60G 17/0195; B60G 2202/135; B60G 2206/11; B60G 21/055; B60G 21/0558
See application file for complete search history.

(56) References Cited

U.S. PATENT DOCUMENTS 2,836,431 A 5/1958 Antoine
2,941,815 A 6/1960 Josef
(Continued)

FOREIGN PATENT DOCUMENTS

DE 2849015 A1 5/1980
DE 102005045177 A1 3/2007
(Continued)

OTHER PUBLICATIONS

European Search Report for EP Application No. 21215569.1, 9 pages, Mailed May 10, 2022.
(Continued)

*Primary Examiner* — Paul N Dickson
*Assistant Examiner* — Tiffany L Webb

(57) ABSTRACT

A sway bar system includes a sway bar having a first end and a second end. The sway bar system further includes a first electronically controlled damper link which is coupled to the first end of the sway bar. The first electronically controlled damper link is coupled a first location of a vehicle. The sway bar system also has a second link which is coupled to the second end of the sway bar. The second link is coupled a second location of the vehicle.

19 Claims, 10 Drawing Sheets

Related U.S. Application Data continuation of application No. 16/144,875, filed on Sep. 27, 2018, now Pat. No. 10,981,429.

(60) Provisional application No. 62/556,022, filed on Sep. 8, 2017.

(51) Int. Cl.

| | | |
|---|---|---|
| *B60G 17/0195* | (2006.01) | |
| *C12N 9/04* | (2006.01) | |
| *C12N 9/10* | (2006.01) | |
| *C12N 15/81* | (2006.01) | |
| *C12P 17/12* | (2006.01) | |
| *F16F 1/14* | (2006.01) | |
| *F16F 9/06* | (2006.01) | |
| *F16F 9/46* | (2006.01) | |
| *F16F 9/56* | (2006.01) | |

(52) U.S. Cl.
CPC ....... *B60G 21/0553* (2013.01); *C12N 9/0006* (2013.01); *C12N 9/1029* (2013.01); *C12N 15/81* (2013.01); *C12Y 101/01248* (2013.01); *C12Y 203/0115* (2013.01); *F16F 1/145* (2013.01); *F16F 9/065* (2013.01); *F16F 9/46* (2013.01); *F16F 9/56* (2013.01); *B60G 2202/135* (2013.01); *B60G 2202/322* (2013.01); *B60G 2204/1224* (2013.01); *B60G 2204/128* (2013.01); *B60G 2204/422* (2013.01); *B60G 2204/4605* (2013.01); *B60G 2204/62* (2013.01); *B60G 2206/11* (2013.01); *B60G 2206/41* (2013.01); *B60G 2300/07* (2013.01); *B60G 2500/20* (2013.01); *B60G 2800/21* (2013.01)

(56) References Cited

U.S. PATENT DOCUMENTS

| | | |
|---|---|---|
| 3,357,512 A | 12/1967 | Wilson |
| 3,602,470 A | 8/1971 | Reynolds |
| 3,871,635 A | 3/1975 | Unruh et al. |
| 3,986,118 A | 10/1976 | Madigan |
| 4,159,756 A | 7/1979 | Murakami et al. |
| 4,183,509 A | 1/1980 | Nishikawa et al. |
| 4,589,528 A | 5/1986 | Axthammer et al. |
| 4,773,671 A | 9/1988 | Inagaki |
| 4,921,080 A | 5/1990 | Lin |
| 4,958,704 A | 9/1990 | Leiber et al. |
| 4,984,819 A | 1/1991 | Kakizaki et al. |
| 5,027,303 A | 6/1991 | Witte |
| 5,035,306 A | 7/1991 | Ashiba |
| 5,105,918 A | 4/1992 | Hagiwara et al. |
| 5,171,036 A | 12/1992 | Ross |
| 5,172,794 A | 12/1992 | Ward |
| 5,186,486 A | 2/1993 | Hynds et al. |
| 5,236,520 A | 8/1993 | Gallagher |
| 5,265,703 A | 11/1993 | Ackermann |
| 5,295,705 A | 3/1994 | Butsuen et al. |
| 5,362,094 A | 11/1994 | Jensen |
| 5,390,949 A | 2/1995 | Naganathan et al. |
| 5,522,280 A | 6/1996 | Bexten |
| 5,597,180 A | 1/1997 | Ganzel et al. |
| 5,630,623 A | 5/1997 | Ganzel |
| 5,952,823 A | 9/1999 | Sprecher et al. |
| 5,987,366 A | 11/1999 | Jun |
| 6,073,536 A | 6/2000 | Campbell |
| 6,244,398 B1 | 6/2001 | Girvin et al. |
| 6,276,693 B1 | 8/2001 | Oakley et al. |
| 6,427,812 B2 | 8/2002 | Crawley et al. |
| 6,457,730 B1 | 10/2002 | Urbach |
| 6,520,510 B1 | 2/2003 | Germain et al. |
| 6,863,291 B2 | 3/2005 | Miyoshi |
| 6,935,157 B2 | 8/2005 | Miller |
| 7,234,714 B2 | 6/2007 | Germain et al. |
| 7,374,028 B2 | 5/2008 | Fox |
| 7,384,053 B1 | 6/2008 | Boecker et al. |
| 7,472,914 B2 | 1/2009 | Anderson et al. |
| 7,484,603 B2 | 2/2009 | Fox |
| 7,997,588 B2 | 8/2011 | Ohnuma et al. |
| 8,220,807 B2 | 7/2012 | Lorenzon et al. |
| 8,550,223 B2 | 10/2013 | Cox et al. |
| 8,627,932 B2 | 1/2014 | Marking |
| 8,807,542 B2 | 8/2014 | Wootten et al. |
| 8,838,335 B2 | 9/2014 | Bass et al. |
| 8,857,580 B2 | 10/2014 | Marking |
| 8,955,653 B2 | 2/2015 | Marking |
| 9,033,122 B2 | 5/2015 | Ericksen et al. |
| 9,120,362 B2 | 9/2015 | Marking |
| 9,239,090 B2 | 1/2016 | Marking et al. |
| 9,303,712 B2 | 4/2016 | Cox |
| 9,353,818 B2 | 5/2016 | Marking |
| 9,452,654 B2 | 9/2016 | Ericksen et al. |
| 9,491,788 B1 | 11/2016 | Kasai et al. |
| 9,623,716 B2 | 4/2017 | Cox |
| 9,682,604 B2 | 6/2017 | Cox et al. |
| 9,797,467 B2 | 10/2017 | Wootten et al. |
| 10,036,443 B2 | 7/2018 | Galasso et al. |
| 10,040,329 B2 | 8/2018 | Ericksen et al. |
| 10,047,817 B2 | 8/2018 | Ericksen et al. |
| 10,060,499 B2 | 8/2018 | Ericksen et al. |
| 10,086,673 B2 * | 10/2018 | Baales ................ B60G 17/056 |
| 10,415,662 B2 | 9/2019 | Marking |
| 10,443,671 B2 | 10/2019 | Marking |
| 10,737,546 B2 | 8/2020 | Tong |
| 10,933,710 B2 | 3/2021 | Tong |
| 10,981,429 B2 | 4/2021 | Tsiaras et al. |
| 11,192,424 B2 * | 12/2021 | Tabata ................ B60G 21/073 |
| 11,634,003 B2 | 4/2023 | Negishi et al. |
| 11,878,678 B2 * | 1/2024 | Krosschell ......... B60G 17/0162 |
| 11,926,189 B2 * | 3/2024 | Tsiaras ..................... F16F 1/145 |
| 2004/0113377 A1 | 6/2004 | Klees |
| 2004/0173985 A1 | 9/2004 | Bruhl et al. |
| 2004/0231904 A1 | 11/2004 | Beck et al. |
| 2005/0077696 A1 | 4/2005 | Ogawa |
| 2007/0235955 A1 | 10/2007 | Mizukoshi et al. |
| 2008/0129000 A1 | 6/2008 | Munday et al. |
| 2008/0203694 A1 | 8/2008 | Gartner et al. |
| 2009/0140501 A1 | 6/2009 | Taylor et al. |
| 2009/0267311 A1 | 10/2009 | Ohnuma et al. |
| 2010/0225084 A1 | 9/2010 | Chapman et al. |
| 2013/0228404 A1 | 9/2013 | Marking |
| 2014/0008160 A1 | 1/2014 | Marking et al. |
| 2014/0224606 A1 | 8/2014 | Baales et al. |
| 2014/0239602 A1 | 8/2014 | Blankenship et al. |
| 2015/0083535 A1 | 3/2015 | Ericksen et al. |
| 2015/0224845 A1 | 8/2015 | Avadhany et al. |
| 2016/0265615 A1 | 9/2016 | Marking |
| 2017/0120713 A1 | 5/2017 | Drozdowski et al. |
| 2017/0129302 A1 | 5/2017 | Jackson |
| 2017/0136842 A1 | 5/2017 | Anderson et al. |
| 2017/0282669 A1 | 10/2017 | Cox et al. |
| 2018/0345747 A1 | 12/2018 | Boon et al. |
| 2019/0100071 A1 | 4/2019 | Tsiaras et al. |
| 2019/0360505 A1 | 11/2019 | Belter et al. |
| 2021/0061052 A1 | 3/2021 | Kim |
| 2021/0086581 A1 | 3/2021 | Smith |
| 2021/0197640 A1 | 7/2021 | Yamashita |
| 2021/0309063 A1 | 10/2021 | Negishi et al. |
| 2021/0309064 A1 | 10/2021 | Negishi et al. |
| 2022/0016949 A1 | 1/2022 | Graus et al. |
| 2022/0134835 A1 | 5/2022 | Izak et al. |
| 2022/0144035 A1 | 5/2022 | Al Sakka et al. |
| 2022/0176769 A1 | 6/2022 | Tong |
| 2022/0194161 A1 | 6/2022 | Negishi et al. |
| 2022/0242186 A1 | 8/2022 | Tong |
| 2022/0242190 A1 | 8/2022 | Stanford et al. |
| 2022/0355638 A1 | 11/2022 | Worley |
| 2023/0113777 A1 | 4/2023 | Vandersmissen et al. |
| 2023/0113819 A1 | 4/2023 | Vandersmissen et al. |
| 2023/0114717 A1 | 4/2023 | Boon et al. |
| 2023/0115594 A1 | 4/2023 | Calchand et al. |
| 2023/0249702 A1 | 8/2023 | Peterson et al. |

(56) References Cited

U.S. PATENT DOCUMENTS

| | | | |
|---|---|---|---|
| 2023/0256785 A1 | 8/2023 | Worley | |
| 2023/0271473 A1* | 8/2023 | Strickland | F16F 9/063 280/124.106 |
| 2023/0294603 A1 | 9/2023 | Dwyer et al. | |

FOREIGN PATENT DOCUMENTS

| | | | |
|---|---|---|---|
| DE | 112005003567 T5 | 3/2008 | |
| DE | 102012006928 A1 | 11/2012 | |
| DE | 202013100681 U1 | 4/2013 | |
| DE | 202013007733 U1 | 10/2013 | |
| DE | 102021104176 A1 | 8/2021 | |
| EP | 0648625 A1 | 4/1995 | |
| EP | 0829383 A2 | 3/1998 | |
| EP | 1000782 A2 | 5/2000 | |
| EP | 1022169 A2 | 7/2000 | |
| EP | 1238833 A1 | 9/2002 | |
| EP | 2123933 A2 | 11/2009 | |
| EP | 1961649 B1 | 12/2010 | |
| EP | 3461663 A1 | 4/2019 | |
| EP | 4112339 A1 | 1/2023 | |
| FR | 2927020 A1 | 8/2009 | |
| FR | 3040331 A1 | 3/2017 | |
| FR | 3101809 A1 | 4/2021 | |
| GB | 2006131 A | 5/1979 | |
| GB | 2343663 A | 5/2000 | |
| GB | 2351951 A | 1/2001 | |
| GB | 2377415 A | 1/2003 | |
| JP | S61146612 A | 7/1986 | |
| JP | H0419210 A | 1/1992 | |
| JP | H04191115 A | 7/1992 | |
| JP | H11165521 A | 6/1999 | |
| JP | 2001105827 A | 4/2001 | |
| JP | 2002264625 A | 9/2002 | |
| JP | 2016211676 A | 12/2016 | |
| WO | 0166969 A1 | 9/2001 | |
| WO | 2016060066 A1 | 4/2016 | |
| WO | 2018215176 A1 | 11/2018 | |
| WO | 2020214666 A1 | 10/2020 | |

OTHER PUBLICATIONS

European Search Report for European Application No. 22215230.8, 9 Pages, Apr. 4, 2023.
European Search Report for European Application No. 23170219.2, 9 Pages, Aug. 22, 2023.
Extended European Search Report for EP Application 22177563.8, dated Nov. 11, 2022, 14 pages.
Extended European Search Report for EP Application 18197941.0 dated Feb. 27, 2019, 11 pages.
Shiozaki, et al., "SP-861—Vehicle Dynamics and Electronic Controlled Suspensions SAE Technical Paper Series No. 910661", International Congress and Exposition, Detroit, Mich., Feb. 25-Mar. 1, 1991.
European Examination Report for EP Application No. 21215569.1, 9 pages, Mailed May 16, 2024.
European Examination Report for EP Application No. 21215569.1, 5 pages, Mailed Jan. 8, 2025.
European Extended Search Report for European Application No. 20879677.1, 8 Pages, Mailed Oct. 23, 2023.
European Search Report for European Application No. 23158363.4, 8 pages, Sep. 6, 2023.
PCT International Search Report for PCT/US2020/056869, 11 Pages, Mailed Jan. 12, 2021.

* cited by examiner

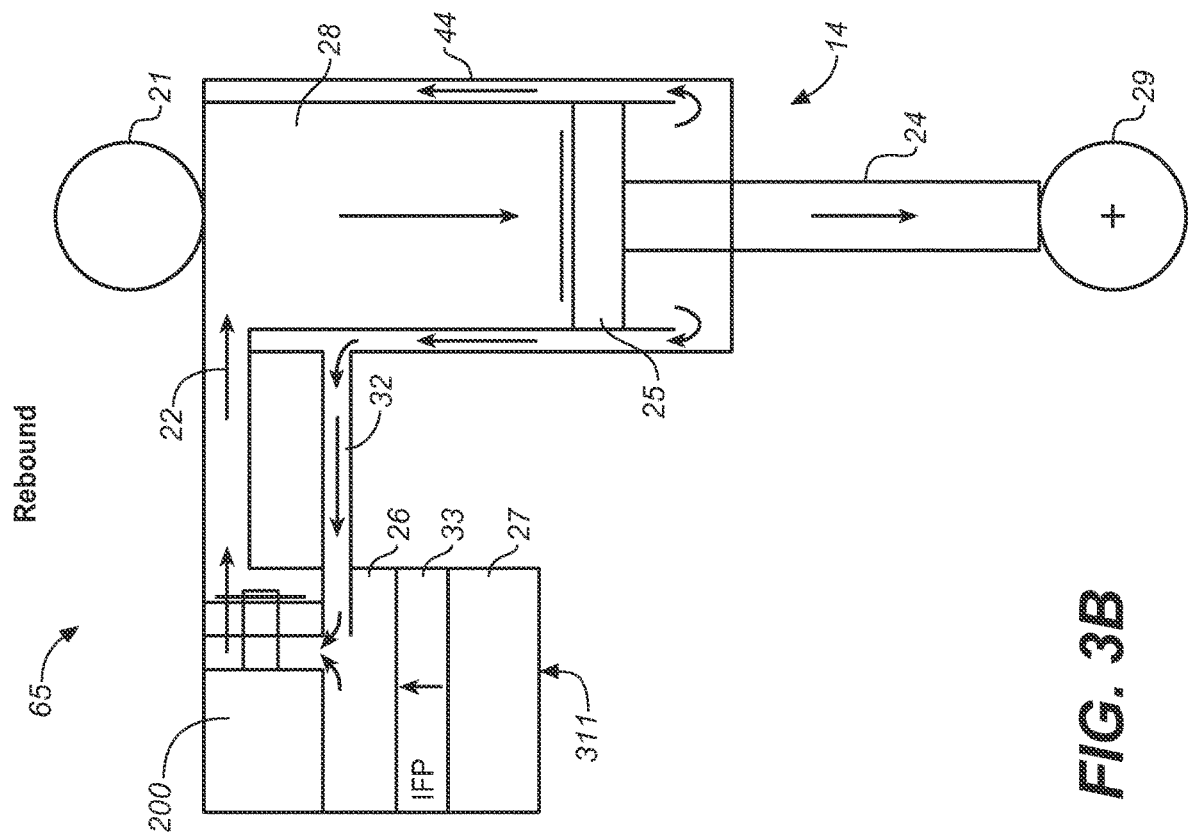
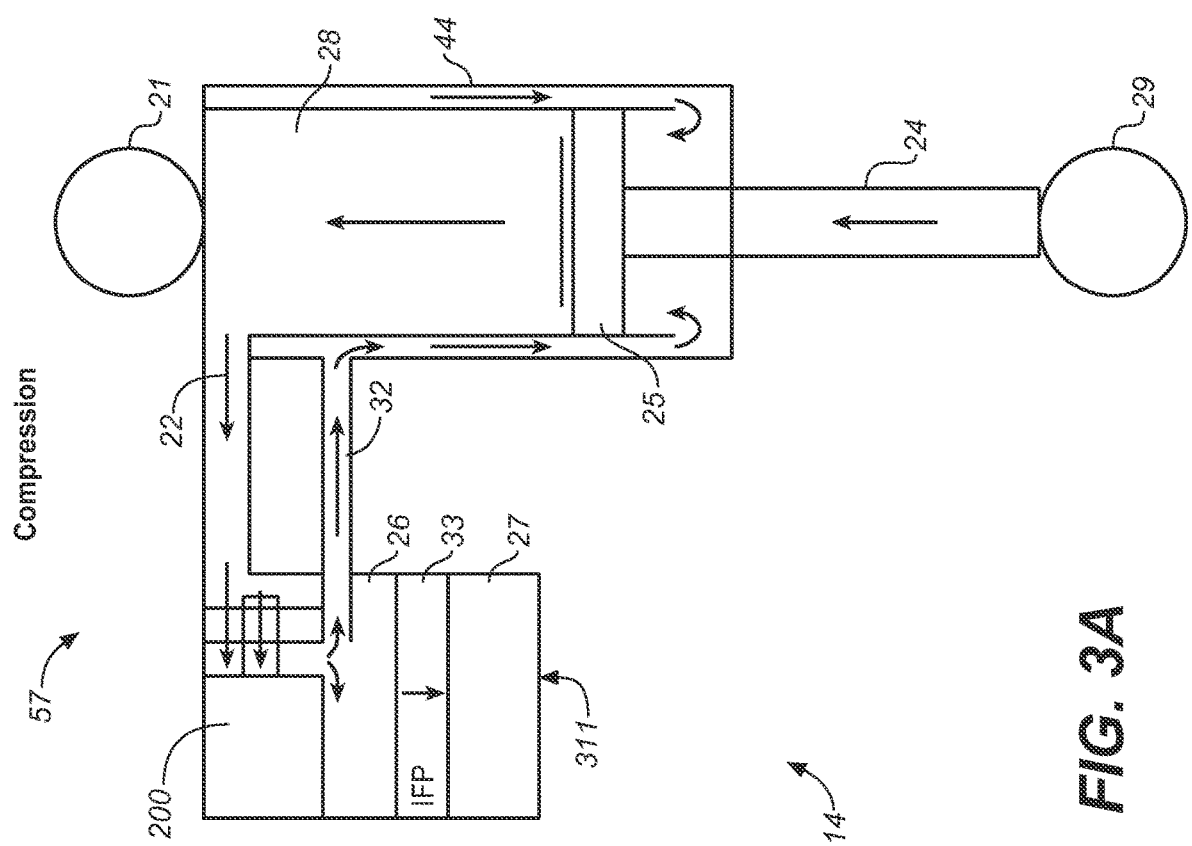
FIG. 3A
FIG. 3B

ELECTRONICALLY CONTROLLED SWAY BAR DAMPING LINK

CROSS-REFERENCE

This application claims priority to and the benefit of co-pending U.S. patent application Ser. No. 17/232,612 filed on Apr. 16, 2021, entitled "ELECTRONICALLY CONTROLLED SWAY BAR DAMPING LINK" by Philip Tsiaras et al, the disclosure of which is hereby incorporated herein by reference in its entirety.

The application Ser. No. 17/232,612 claims priority to and the benefit of U.S. patent application Ser. No. 16/144,875 filed on Sep. 27, 2018, now U.S. Issued U.S. Pat. No. 10,981,429, entitled "ELECTRONICALLY CONTROLLED SWAY BAR DAMPING LINK" by Philip Tsiaras et al, the disclosure of which is hereby incorporated herein by reference in its entirety.

The application Ser. No. 16/144,875 claims priority to and the benefit of U.S. Provisional Patent Application 62/566,022 filed on Sep. 29, 2017, entitled "ELECTRONICALLY CONTROLLED SWAY BAR DAMPING LINK" by Philip Tsiaras et al, the disclosure of which is hereby incorporated herein by reference in its entirety.

FIELD OF THE INVENTION

Embodiments of the present technology relate generally to sway bar on a vehicle.

BACKGROUND

A sway bar (anti-sway bar, roll bar, anti-roll bar, stabilizer bar) is a part of an automobile suspension that reduces the body roll of a vehicle. The sway bar is basically a torsion spring that resists body roll motions. Often, it is formed from a cylindrical steel bar patterned in a "U" shape. A conventional sway bar assembly includes a sway bar and also includes two end links. Typically, the first of the two end links is flexibly coupled to one end of the sway bar, and the second of the two ends links flexibly coupled to the other end of the sway bar. Each of the two end links are then connected to a location on the vehicle near a wheel or axle at respective left and right sides of the suspension for the vehicle. As a result, when the left and right sides of the suspension move together, the sway bar rotates about its mounting points. However, when the left and right sides of the suspension move relative to one another, the sway bar is subjected to torsion and forced to twist. The twisting of the sway bar transfers the forces between a heavily-loaded suspension side (the side of the vehicle subjected to more roll movement force than the other side of the vehicle) to the opposite, lesser-loaded, suspension side (the side of the vehicle subjected to lesser roll movement force than the other side of the vehicle).

BRIEF DESCRIPTION OF THE DRAWINGS

Aspects of the present invention are illustrated by way of example, and not by way of limitation, in the accompanying drawings, wherein:

FIG. 3A is a cutaway schematic view of a twin tube electronically controlled damper link in compression, in accordance with an embodiment of the present invention.

FIG. 3B is a cutaway schematic view of a twin tube electronically controlled damper link in rebound, in accordance with an embodiment of the present invention.

Figure 1A:
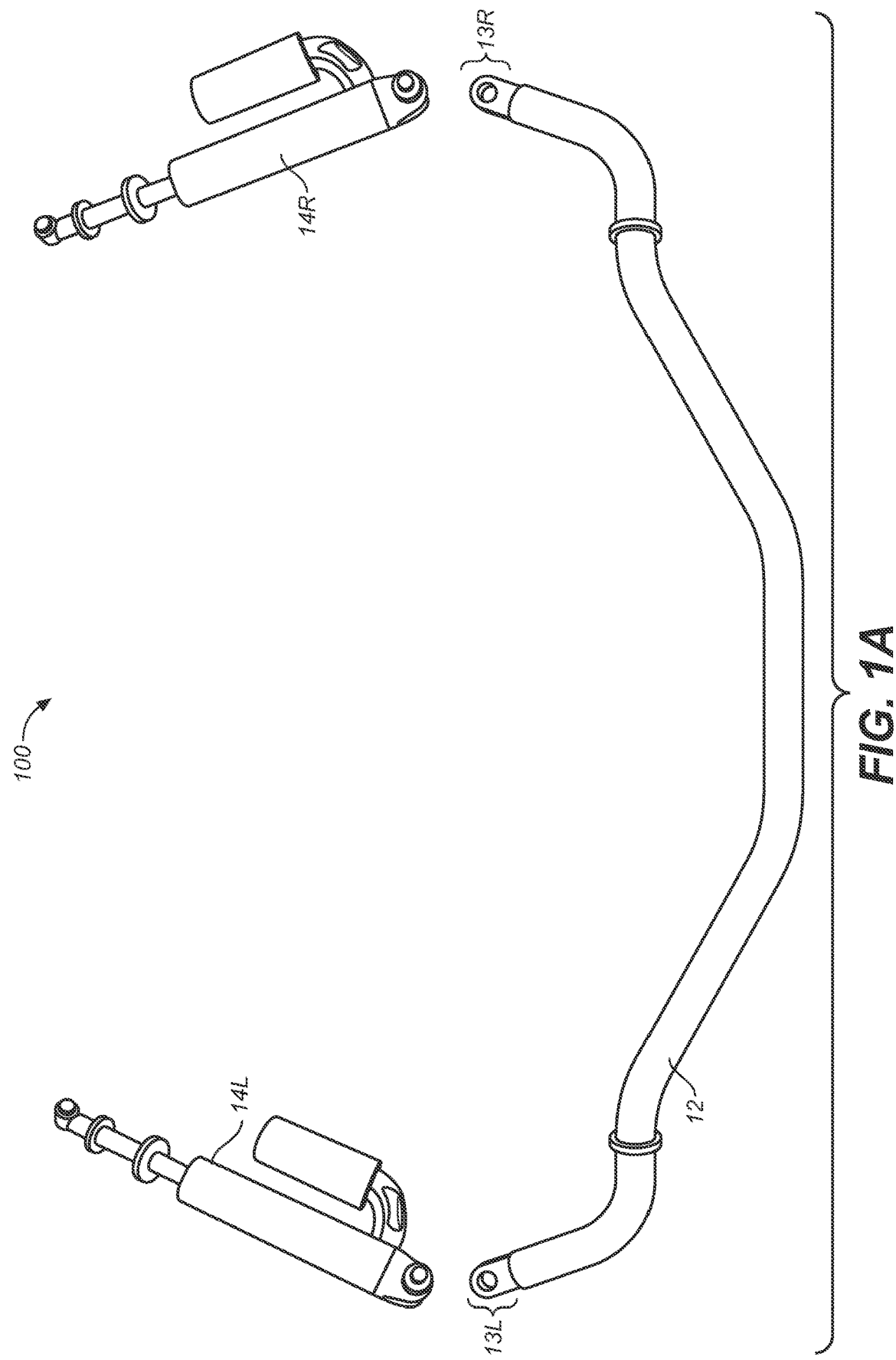
FIG. 1A is a perspective view of a sway bar system including at least one electronically controlled damper link, in accordance with an embodiment of the present invention.

The drawings referred to in this description should be understood as not being drawn to scale except if specifically noted.

DESCRIPTION OF EMBODIMENTS

The detailed description set forth below in connection with the appended drawings is intended as a description of various embodiments of the present invention and is not intended to represent the only embodiments in which the present invention is to be practiced. Each embodiment described in this disclosure is provided merely as an example or illustration of the present invention, and should not necessarily be construed as preferred or advantageous over other embodiments. In some instances, well known methods, procedures, objects, and circuits have not been described in detail as not to unnecessarily obscure aspects of the present disclosure.

In the following discussion, embodiments of the present sway bar system (also referred to herein as an "E-Sway Bar" system) are described in detail. As will be described below, embodiments of the present sway bar system advantageously enable remote input (e.g., manual remote input or automatic remote input) to manipulate the stiffness of the present sway bar system. The stiffness of the sway bar system can be thought of as, for example, a driver's (or passenger's) perception of the "roll stability" of the vehicle. In other words, the perception of the driver (or passenger) of the vehicle for the vehicle to resist or allow "roll motion".

As one example, when riding in a vehicle (e.g., a sports car) which appears to provide significant resistance to a rolling motion of the vehicle, it can be said that the vehicle has a "stiff" sway bar system. As another example, when riding in a vehicle (e.g., a motorhome or bus) which appears to not provide significant resistance to a rolling motion of the vehicle, it can be said that the vehicle has a "soft" sway bar system. It will be understood that a "soft" sway bar system is desired in various conditions. For example, a soft sway bar system provides better comfort during rock crawling and some slow driving activities. Further, it will be understood that "stiff" sway bar system is desired in various conditions. For example, it will be understood that a stiff sway bar system provides increased handling and control during high speed cornering and various racing activities.

Further, in the following discussion, the term "active", as used when referring to a valve or damping component, means adjustable, manipulatable, etc., during typical operation of the valve. For example, an active valve can have its operation changed to thereby alter a corresponding damping characteristic from a "soft" damping setting to a "firm" damping setting by, for example, adjusting a switch in a passenger compartment of a vehicle. Additionally, it will be understood that in some embodiments, an active valve may also be configured to automatically adjust its operation, and corresponding damping characteristics, based upon, for example, operational information pertaining to the vehicle and/or the suspension with which the valve is used. Similarly, it will be understood that in some embodiments, an active valve may be configured to automatically adjust its operation, and corresponding damping characteristics, to provide damping based upon received user input settings (e.g., a user-selected "comfort" setting, a user-selected "sport" setting, and the like). Additionally, in many instances, an "active" valve is adjusted or manipulated electronically (e.g., using a powered solenoid, or the like) to alter the operation or characteristics of a valve and/or other component. As a result, in the field of suspension components and valves, the terms "active", "electronic", "electronically controlled", and the like, are often used interchangeably.

In the following discussion, the term "manual" as used when referring to a valve or damping component means manually adjustable, physically manipulatable, etc., without requiring disassembly of the valve, damping component, or suspension damper which includes the valve or damping component. In some instances, the manual adjustment or physical manipulation of the valve, damping component, or suspension damper, which includes the valve or damping component, occurs when the valve is in use. For example, a manual valve may be adjusted to change its operation to alter a corresponding damping characteristic from a "soft" damping setting to a "firm" damping setting by, for example, manually rotating a knob, pushing or pulling a lever, physically manipulating an air pressure control feature, manually operating a cable assembly, physically engaging a hydraulic unit, and the like. For purposes of the present discussion, such instances of manual adjustment/physical manipulation of the valve or component can occur before, during, and/or after "typical operation of the vehicle".

It should further be understood that a vehicle suspension may also be referred to using one or more of the terms "passive", "active", "semi-active" or "adaptive". As is typically used in the suspension art, the term "active suspension" refers to a vehicle suspension which controls the vertical movement of the wheels relative to vehicle. Moreover, "active suspensions" are conventionally defined as either a "pure active suspension" or a "semi-active suspension" (a "semi-active suspension" is also sometimes referred to as an "adaptive suspension"). In a conventional "pure active suspension", a motive source such as, for example, an actuator, is used to move (e.g. raise or lower) a wheel with respect to the vehicle. In a "semi-active suspension", no motive force/actuator is employed to adjust move (e.g. raise or lower) a wheel with respect to the vehicle. Rather, in a "semi-active suspension", the characteristics of the suspension (e.g. the firmness of the suspension) are altered during typical use to accommodate conditions of the terrain and/or the vehicle. Additionally, the term "passive suspension", refers to a vehicle suspension in which the characteristics of the suspension are not changeable during typical use, and no motive force/actuator is employed to adjust move (e.g. raise or lower) a wheel with respect to the vehicle. As such, it will be understood that an "active valve", as defined above, is well suited for use in a "pure active suspension" or a "semi-active suspension".

In some embodiments of the present invention, the damping characteristic of at least one damper is obtained by controlling a remotely adjustable active valve (may also be referred to as a remotely adjustable electronic valve or, more concisely, as just an active valve) of the damper, wherein the remotely adjustable active valve utilizes a relatively small solenoid (using relatively low amounts of power) to generate relatively large damping forces. Examples of such an active valve are described and shown in U.S. Pat. Nos. 9,120,362; 8,627,932; 8,857,580; 9,033,122; and 9,239,090 which are incorporated herein, in their entirety, by reference.

Referring now to FIG. 1A, a perspective view of a sway bar system 100 including a sway bar 12 and two electronically controlled damper links, 14L and 14R, is shown in accordance with an embodiment of the present invention. For purposes of clarity, in FIG. 1A, electronically controlled damper link 14L and electronically controlled damper link 14R are shown slightly separated from sway bar 12 in order to more clearly depict the location, 13L, where electronically controlled damper link 14L couples to sway bar 12, and to more clearly depict the location, 13R, where electronically controlled damper link 14R couples to sway bar 12. In various embodiments of present sway bar system 100, an upper portion of electronically controlled damper link 14L includes a bushing, or similar coupling feature, to readily enable coupling of electronically controlled damper link 14L to, for example, 13L of sway bar 12. Similarly, in various embodiments of present sway bar system 100, an upper portion of electronically controlled damper link 14R includes a bushing, or similar coupling feature, to readily enable coupling of electronically controlled damper link 14R to, for example, 13R of sway bar 12. It should be noted that present sway bar system 100 is not limited solely to the use of a bushing for coupling one or both of electronically controlled damper link 14L and electronically controlled damper link 14R to sway bar 12.

With reference still to FIG. 1A, in various embodiments of present sway bar system 100, a lower portion of electronically controlled damper link 14L includes an eyelet, or similar coupling feature, to readily enable coupling of electronically controlled damper link 14L to a location on a vehicle. Similarly, in various embodiments of present sway bar system 100, a lower portion of electronically controlled damper link 14R includes an eyelet, or similar coupling feature, to readily enable coupling of electronically controlled damper link 14R to a location on a vehicle. It should be noted that present sway bar system 100 is not limited solely to the use of an eyelet for coupling one or both of electronically controlled damper link 14L and electronically controlled damper link 14R to a vehicle.

Although the embodiment of FIG. 1A, depicts sway bar system 100 having two electronically controlled damper links 14L and 14R, in another embodiment of the present invention, sway bar system 100 includes only a single electronically controlled damper link (e.g., only 14L or only 14R). In such an embodiment, an electronically controlled damper link (e.g., 14L or 14R) is coupled to one end (e.g., a first end) of sway bar 12, and, for example, a conventional end link is coupled to the other end (e.g., a second end) of sway bar 12. Hence, sway bar system 100 of the present invention is well suited to embodiments in which one end of sway bar 12 has an electronically controlled damper link (e.g., 14L or 14R) coupled thereto, and also to embodiments in which both ends of sway bar 12 have an electronically controlled damper link (e.g., 14L and 14R, respectively) coupled thereto. Additionally, for purposes of conciseness and clarity, portions of the following description may refer to an electronically controlled damper link as "electronically controlled damper link 14", instead repeating the same description for each of electronically controlled damper link 14L and electronically controlled damper link 14R. It should be noted that such portions of the description are applicable to either electronically controlled damper link 14L or electronically controlled damper link 14R, as shown in sway bar system 100 of FIG. 1A. Further, the present description will pertain to embodiments in which one end of sway bar 12 has an electronically controlled damper electronically controlled damper link (e.g., 14L or 14R) coupled thereto, and also to embodiments in which both ends of sway bar 12 have an electronically controlled damper link (e.g., 14L and 14R, respectively) coupled thereto.

Figure 1B:
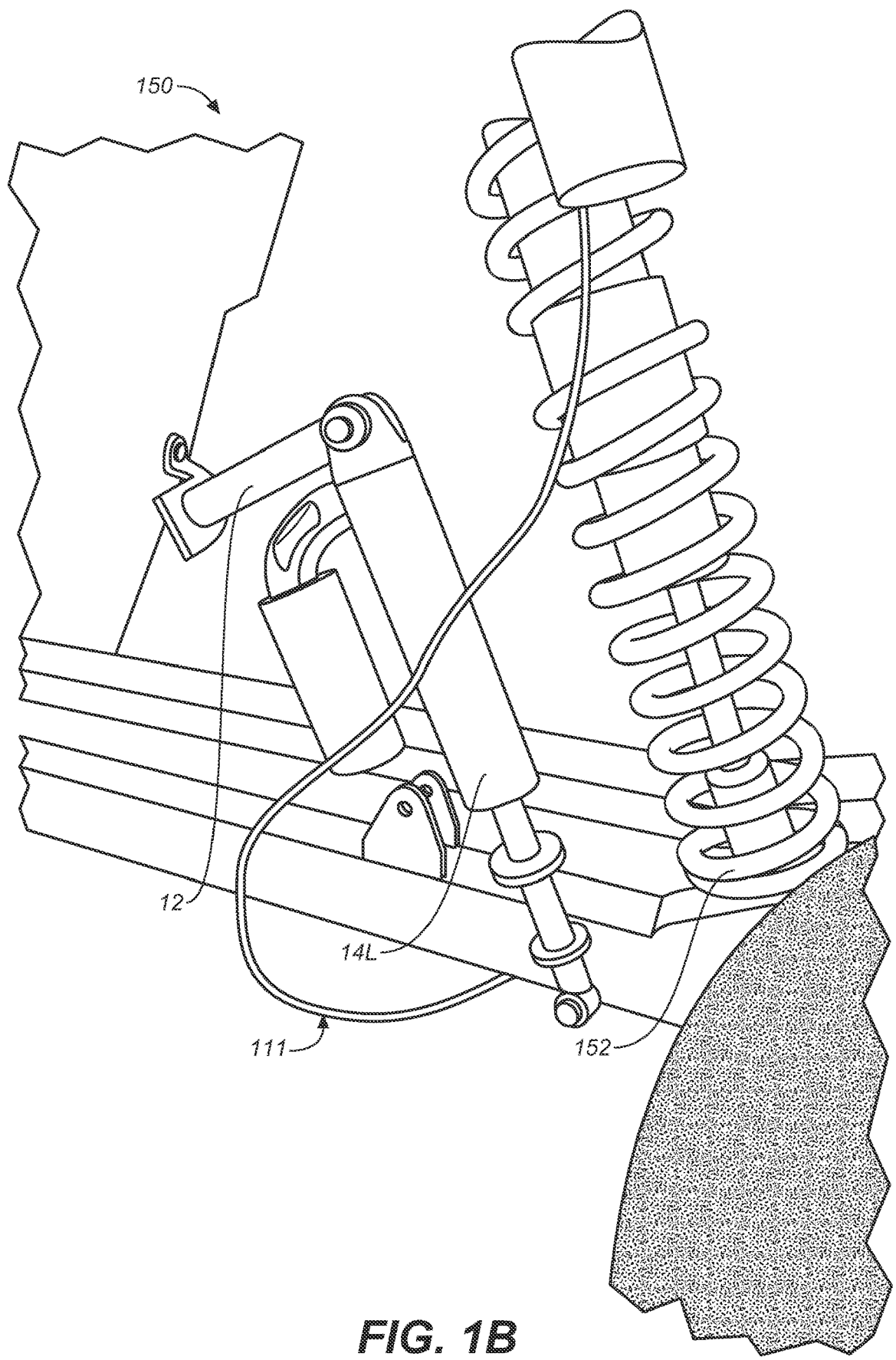
FIG. 1B is a perspective view of a sway bar system including at least one electronically controlled damper link installed in a vehicle, in accordance with an embodiment of the present invention.

With reference now to FIG. 1B, a perspective view 150 is provided of sway bar system 100, of FIG. 1A, installed in a vehicle, in accordance with an embodiment of the present invention. In the embodiment of FIG. 1B, sway bar 12 and at least one electronically controlled damper link 14L is shown installed in a vehicle 152. In embodiments of the present invention, sway bar system 100 is coupled to a vehicle with at least one end of sway bar 12 coupled to the vehicle by an electronically controlled damper link (e.g., 14L or 14R). That is, unlike conventional sway bar assemblies, in embodiments of the present invention, sway bar system 100 has one end of sway bar 12 coupled to a vehicle by an electronically controlled damper link (e.g., 14L or 14R). In other embodiments of the present invention, sway bar system 100 has both ends of sway bar 12 coupled to a vehicle by an electronically controlled damper link (e.g., 14L and 14R, respectively). As a result, and as will be described further below, the "stiffness" provided by sway bar system 100 can be remotely controlled by controlling the stiffness or compliance of one or both of electronically controlled damper links 14L and 14R coupling sway bar 12 to a vehicle. Importantly, FIG. 1B further shows a cable 111. Cable 111 is used to provide input to electronically controlled damper link 14. Such input is used to control the damping characteristics of electronically controlled damper link 14. In various embodiments, as are described below in detail, such input may consist of electrical input (based upon, e.g., user input, sensors-derived data, or any of various other sources) used to control an electronic valve within electronically controlled damper link 14 and, correspondingly, control the damping characteristics of electronically controlled damper link 14. Embodiments of the present sway bar system 100 are also well suited to using a wireless signal (in addition to, or in lieu of, cable 111) to control a valve or other component of electronically controlled damper link 14 such that, ultimately, the damping characteristic of electronically controlled damper link 14 is controllable.

Figure 1C:
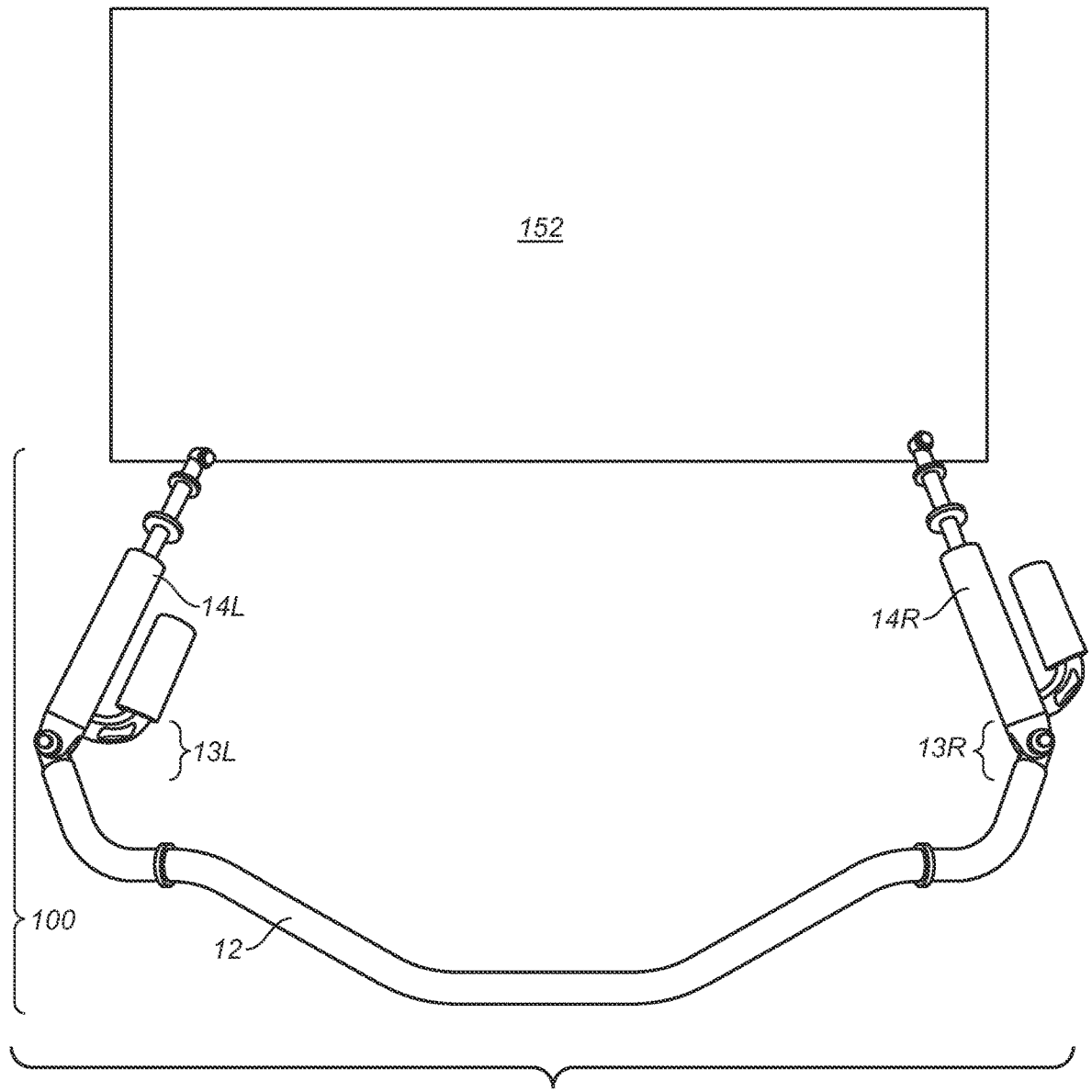
FIG. 1C is a perspective view of a sway bar system including two electronically controlled damper links coupled to a vehicle, in accordance with an embodiment of the present invention.

Referring now to FIG. 1C, a perspective view is provided of sway bar system 100 having electronically controlled damper link 14L coupled to a first end of sway bar 12 at location 13L. In the embodiment of FIG. 1C, sway bar system 100 further includes electronically controlled damper link 14R coupled to a second end of sway bar 12 at location 13R. Additionally, as schematically depicted in FIG. 1C, in the present embodiment, electronically controlled damper link 14L is coupled to vehicle 152, and electronically controlled damper link 14R is coupled to vehicle 152. In various embodiments of the present invention, electronically controlled damper link 14L and electronically controlled damper link 14R are coupled to vehicle 152 at a location, for example, near a wheel or axle of vehicle 152 at respective left and right sides of vehicle 152. It will be understood that when the left and right sides of the suspension of vehicle 152 move relative to one another, sway bar 12 of sway bar system 100 is subjected to torsion and forced to twist. The twisting of sway bar 12 will transfer forces between a heavily-loaded suspension side of vehicle 152 to the opposite, lesser-loaded, suspension side of vehicle 152.

Figures 2A, 2B:
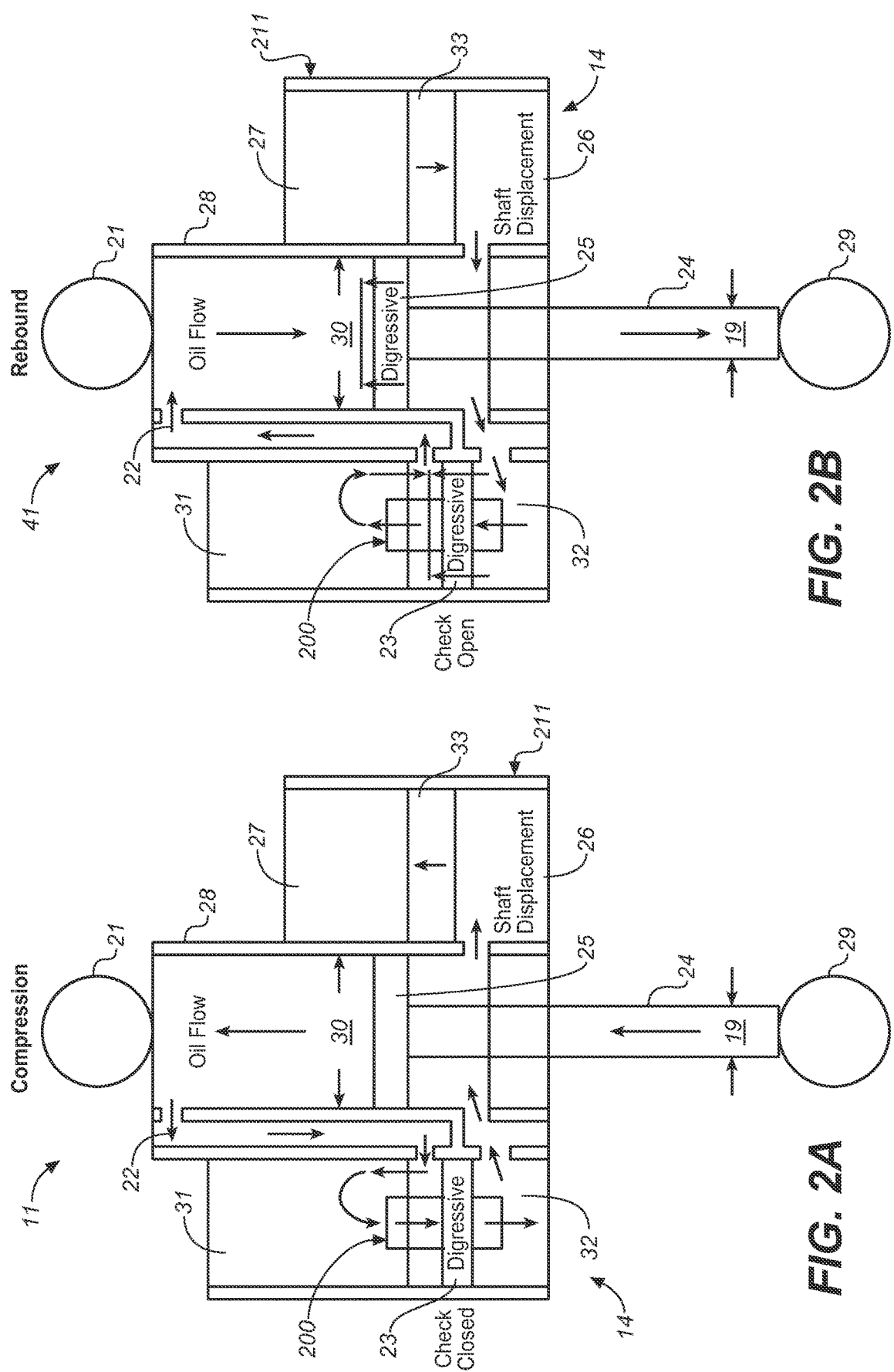
FIG. 2A is a cutaway schematic view of an electronically controlled damper link in a state of compression, in accordance with an embodiment of the present invention.
FIG. 2B is a cutaway schematic view of an electronically controlled damper link in a state of rebound, in accordance with an embodiment of the present invention.

Referring now to FIG. 2A, a cutaway schematic view 11 of electronically controlled damper link 14 in a state of compression is shown, in accordance with an embodiment of the present invention. Referring also to FIG. 2B, a cutaway schematic view 41 of electronically controlled damper link 14 in a state of rebound is shown, in accordance with an embodiment of the present invention. As FIG. 2A and FIG. 2B are similar, other than their state of operation (compression in FIG. 2A and rebound in FIG. 2B), the components of FIG. 2A and FIG. 2B will be discussed at the same time. However, it should be appreciated that various fluid flow through various valves and components of electronically controlled damper link 14 may be in an opposite direction in FIG. 2A when compared to FIG. 2B. Further, it will be understood that the location of certain "inlet valves" or "outlet valves", and the applicability of terms such as "inlet" or "outlet", and the like, as applied to the various valves and/or components, may vary in FIG. 2A when compared to FIG. 2B.

Referring again to FIG. 2A and also to FIG. 2B, electronically controlled damper link 14 includes a damper cylinder 28 with a shaft 24 and a damping piston 25. As shown, in FIG. 2A, shaft 24 and damping piston 25 are coupled to each other. It will be understood that, typically, damper cylinder 28 encloses a damper cylinder chamber (sometimes referred to as the damper cylinder volume). It will further be understood that damping piston 25 and shaft 24 are, typically, movable into and out of the damper cylinder chamber and that damping piston 25 and shaft 24 move axially with respect to damper cylinder 28. Damper cylinder 28 is typically at least partially filled with a damping fluid. As will be understood, during operation of the damper, the damping fluid is metered from one side of damping piston 25 to the other side by passing through valve flow opening 22 traversing through valve 200 (which is described in detail below) and, optionally, through openings in digressive piston 23. In one such embodiment, openings are formed in damping piston 25. It should be noted that for purposes of clarity, valve 200 is depicted schematically in FIG. 2A, FIG. 2B, FIG. 3A and FIG. 3B. A detailed illustration of at least one embodiment of valve 200 is provided at FIG. 5, FIG. 6 and FIG. 7. Similarly, a detailed description of at least one embodiment of valve 200 is provided below and in conjunction with the discussion of FIG. 5, FIG. 6 and FIG. 7. Additionally, although valve 200 is referred to as a single valve, embodiments of the present invention are also well suited to the use of more than one valve to comprise "valve 200". For purposes of brevity and clarity, however, the present discussion will refer to a valve 200 as a single valve.

In embodiments of sway bar system 100, fluid flow through various openings within the electronically controlled damper 14 is restricted using, for example, shims which partially obstruct the flow paths in each direction in digressive piston 23 and also available flow paths in damping piston 25. By selecting shims having certain desired stiffness characteristics, the dampening effects caused by digressive piston 23 can be increased or decreased and dampening rates can be different between the compression and rebound strokes of damping piston 25. For example, the shims are configured to meter rebound flow from the rebound portion of the to the compression portion of damper cylinder 28, or to meter compression flow from the compression portion of damper cylinder 28 to the rebound portion. Embodiments of the present invention are well suited to metering fluid flow during compression, during rebound, or during both compression and rebound.

A fluid reserve cylinder 211 is in fluid communication with the damper cylinder 28 for receiving and supplying damping fluid as shaft 24 moves in and out of damper cylinder 28. Fluid reserve cylinder 211 is in fluid communication with damper cylinder 28 via a fluid path 32. As illustrated, for example, in FIG. 2A and FIG. 2B, fluid reserve cylinder 211 at least partially encloses a fluid reservoir chamber 26 and a gas chamber 27. As also shown in FIG. 2A and FIG. 2B, fluid reserve cylinder 211 also includes and encloses an internal floating piston (IFP) 33. IFP 33 is disposed within fluid reserve cylinder 211 and movably and fluidly separates fluid reservoir chamber 26 and gas chamber 27. IFP 33 can be described as having gas chamber 27 on the "backside" thereof (sometimes referred to as the "blind end" of IFP 33). Additionally, IFP 33 can also be described as having fluid reservoir chamber 26 on the "frontside" thereof.

With reference still to FIG. 2A and FIG. 2B, it will be understood that gas within gas chamber 27 is compressible as fluid reservoir cylinder 26 (on the "frontside" of IFP 33) fills with damping fluid due to movement of shaft 24 and damping piston 25 into damper cylinder 28. Certain features of reservoir-type dampers are shown and described in U.S. Pat. No. 7,374,028, which is incorporated herein, in its entirety, by reference. As described above, in various embodiments, sway bar system 100 will have an upper portion of electronically controlled damper 14 coupled to sway bar 12 through the use of a bushing. Similarly, in various embodiments, a lower portion of upper portion of electronically controlled damper 14 (e.g., a portion of shaft 24 (opposite damping piston 25) which extends outside of damper cylinder 28) is supplied with an eyelet 29 to readily enable coupling of electronically controlled damper 14 to a part of the vehicle. As a result, as shaft 24 and damping piston 25 move into damper cylinder 28 (e.g., during compression), depending upon the setting of the valve 200, the damping fluid can control the relative speed of movement between sway bar 12 and the vehicle mounting location. Specifically, the incompressible damping fluid moving through the various flow paths provided in the damping piston 25 and/or the metered bypass 44 (see for example FIGS. 3A and 3B), as will be described herein, can be used to control the damping characteristics of electronically controlled damper 14. In one example, as shaft 24 and damping piston 25 move out of the damper cylinder 28 (e.g., during extension or "rebound") damping fluid is metered through the flow path 32, valve flow opening 22, and valve 200, and the flow rate and corresponding stiffness of electronically controlled damper 14 is thereby controlled. Once again, it should be noted that embodiments of the present invention are well suited to metering fluid flow during compression, during rebound, or during both compression and rebound. Further, it should be noted that embodiments of the present invention are also well suited to various other structures and arrangements including, but not limited to, main piston damping, piston bypass configurations, and various other damper configurations.

Referring now to FIG. 3A, a cutaway schematic view 57 of a twin tube electronically controlled damper link 14 in a compression state is shown in accordance with an embodiment of the present invention. Similarly, as above, FIG. 3B is a cutaway schematic view 65 of a twin tube electronically controlled damper link 14 in a rebound state is shown in accordance with an embodiment of the present invention. As such, the components of FIGS. 3A and 3B will be discussed at the same time (and those components that overlap with FIG. 2A or 2B will not be re-addressed). However, it should be appreciated that the fluid flow through valve 200 will be in the opposite direction when comparing FIGS. 3A and 3B. Thus, for example, there may be an inlet valve in one location, and an outlet valve at different location, or a valve that can operate as both an inlet and an outlet.

In general, the twin tube structure, of FIG. 3A and FIG. 3B, allows the bypass 44 to provided fluid connectivity between the lower portion of damper cylinder 28 below damping piston 25 and the upper portion of damper cylinder 28 above damping piston 25 (as oriented).

In one embodiment, the valve 200 is a remotely and electronically controlled valve. In one such embodiment, the control of valve 200 is made from a remote location such as in the cab of the vehicle to which sway bar system 100 is coupled.

As will be described in detail below, valve 200 of electronically controlled damper link 14 allows for fast acting, proportional changes to compression and/or rebound damping rates. Moreover, the damping of electronically controlled damper link 14 can vary from fully locked out to a compliant state. Thus, electronically controlled damper link 14 replaces a conventional end link. By providing fast acting, proportional changes to compression and rebound damping, electronically controlled damper link 14 is significantly superior in performance and operation to a conventional end link device. Furthermore, electronically controlled damper link 14 enables the stiffness or compliance of sway bar system 100 to be remotely controlled by controlling the stiffness or compliance of electronically controlled damper link 14. For example, in various embodiments of the present invention, electronically controlled damper link 14 will, for example, increase its dampening, and, correspondingly, increase the stiffness of sway bar system 100. In various embodiments of the present invention, such increased stiffness of sway bar system 100 is advantageous, for example, during cornering, as vehicle speed rises, when vehicle roll is detected, and the like.

Conversely, in various embodiments of the present invention, electronically controlled damper link 14 will, for example, decrease its dampening, and, correspondingly, decrease the stiffness of sway bar system 100. In various embodiments of the present invention, such decreased stiffness of sway bar system 100 is advantageous, for example, for rough terrain, slow speeds, rock crawling, and the like.

Moreover, in various embodiments of sway bar system 100, adjustments are made to electronically controlled damper link 14 to obtain a stiff or soft sway bar feel, wherein such a "sway bar feel" is selectable by the rider and/or driver of the vehicle to which sway bar system 100 is coupled. Additionally, in various embodiments of sway bar system 100, settings are used to control understeer/oversteer, etc. For example, there may be a number of presets that an operator of the vehicle, to which sway bar system 100 is coupled, can select to adjust the damping characteristics of electronically controlled damper link 14 based on the terrain being covered, the speed being driven, and the like. Further, in various embodiments of the present sway bar system, such presets are selectable and changeable on the fly, e.g., throughout a drive, without the operator having to stop the vehicle.

In one embodiment of sway bar system 100, the damping characteristics of electronically controlled damper link 14 are automatically adjusted by a processor and are based on one or more inputs received at the processor. For example, in one embodiment of sway bar system 100, steering inputs, vehicle roll, speed, terrain, and the like are detected and/or monitored via one or more sensors on or about the vehicle to which sway bar system 100 is coupled. Sensors which are utilized to monitor various parameters include, but not limited to, accelerometers, sway sensors, suspension changes, visual identification technology (e.g., single or multi spectrum cameras), driver input monitors, steering wheel turning sensors, and the like.

For example, one embodiment of sway bar system 100 uses an inertial measurement unit (IMU) to sense rough terrain. One embodiment of sway bar system 100 has an attitude and heading reference system (AHRS) that provides 3D orientation integrating data coming from inertial gyroscopes, accelerometers, magnetometers and the like. For example, in yet another embodiment of sway bar system 100, the AHRS is a GPS aided Microelectromechanical systems (MEMS) based IMU and static pressure sensor. It should be noted that in various embodiments of sway bar system 100, various sensor-derived data, user input, IMU data, AHRS data, and the like, is ultimately used (e.g., by passing a corresponding signal through cable 111 of FIG. 1B to electronically controlled damper link 14) to control the damping characteristics of electronically controlled damper link 14.

As discussed herein, electronically controlled damper link 14 includes IFP 33 which, in one embodiment of sway bar system 100, is placed on the rebound side to create more compression damping without causing cavitation. When a check valve opens, the damping force of electronically controlled damper link 14 will be lower thereby reducing the chances of cavitation.

In one embodiment of sway bar system 100, by reducing the diameter (see e.g., reference number 19 of FIG. 2A and FIG. 2B) of shaft 24, reaction forces of shaft 24 will also be reduced. Additionally, in embodiments of sway bar system 100, the diameter of damper cylinder 28 is reduced. By reducing the diameter of damper cylinder 28, the damper cylinder volume corresponding to damper cylinder 28 is also reduced. Hence, changes in the diameter of damper cylinder 28 ultimately alter the ratio between the damper cylinder volume of damper cylinder 28 and the flow area of, for example, valve 200. Reducing the damper cylinder volume with respect to the flow area of valve 200 will provide a softer initial pressure setting in gas chamber 27.

In various embodiments of sway bar system 100, damping characteristics of electronically controlled damper link 14 are altered by changing a damping fluid flow path. As one example, depending upon the type of valve 200, flow path 32 can be changed. For example, the damping fluid flow path in a twin tube embodiment (see, e.g., FIG. 3A and FIG. 3B) is different from the damping fluid flow path in a non-twin tube embodiment (see, e.g., FIG. 2A and FIG. 2B).

In various embodiments of sway bar system 100, damping characteristics of electronically controlled damper link 14 are altered by selectively controlling the flow of damping fluid through damping piston 25. For example, in one embodiment, electronically controlled damper link 14 includes a damping piston 25 which is a solid piston with no valving therethrough (as shown in FIG. 2A). However, in another embodiment of sway bar system 100, electronically controlled damper link 14 includes a damping piston 25 which is a digressive piston (as shown in FIG. 2B). In an embodiment of sway bar system 100 as depicted in FIG. 2B, by having a digressive piston on both the base valve and damping piston 25, a better high speed blow off is achieved.

Figure 4:
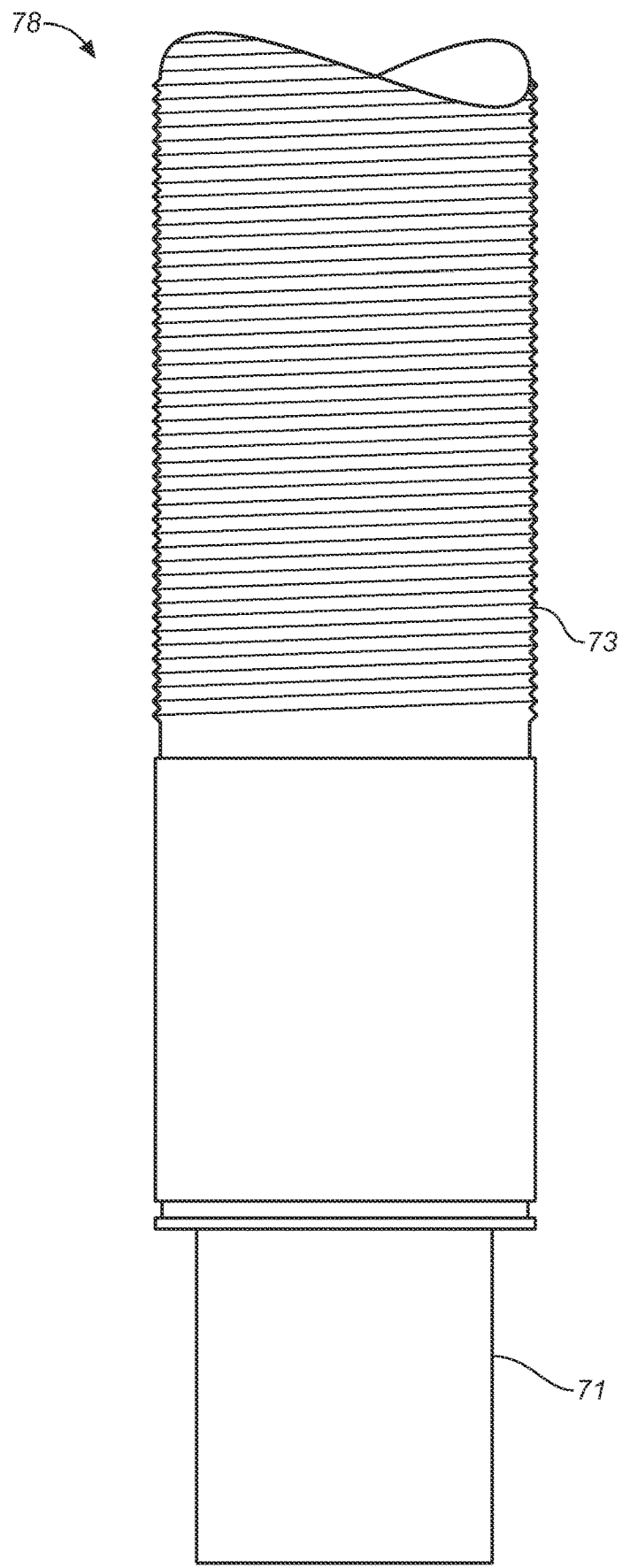
FIG. 4 is a perspective view of an inner body portion of a first damper cylinder within a larger outer body portion of a second damper cylinder, in accordance with an embodiment of the present invention.

Referring now to FIG. 4 (and also to FIG. 1A), as stated above, in embodiments of sway bar system 100, the diameter of damper cylinder 28 is reduced. By reducing the diameter of damper cylinder 28, the damper cylinder volume corresponding to damper cylinder 28 is also reduced. Hence, changes in the diameter of damper cylinder 28 ultimately alter the ratio between the damper cylinder volume of damper cylinder 28 and the flow area of, for example, valve 200. In FIG. 4 (and also referring to FIG. 2A and FIG. 2B), a perspective view 78 of an inner body portion of a first damper cylinder 71 within a larger outer body portion of a second damper cylinder 73 is shown in accordance with an embodiment of the present invention. In other words, the damper cylinder diameter 30 of damper cylinder 28 is reduced by fitting a smaller damper cylinder (e.g., first damper cylinder 71) inside of the larger damper cylinder (e.g., second damper cylinder 73). A new body cap and seal head is then used to attach damper cylinder 71 and damper cylinder 73.

In one embodiment, shaft size 19 of shaft 24 is also reduced. The change in damper cylinder diameter 30 changes the ratio between damper cylinder volume and the flow area of valve 200. For example, when valve 200 remains the same and damper cylinder volume is decreased, electronically controlled damper link 14 will have a softer decoupled setting. In various embodiments of sway bar system 200, the ratio of damper cylinder volume of damper cylinder 28 to the flow area of valve 200 can be tuned by changing one or both of damper cylinder volume and the flow area of valve 200.

Figure 5:
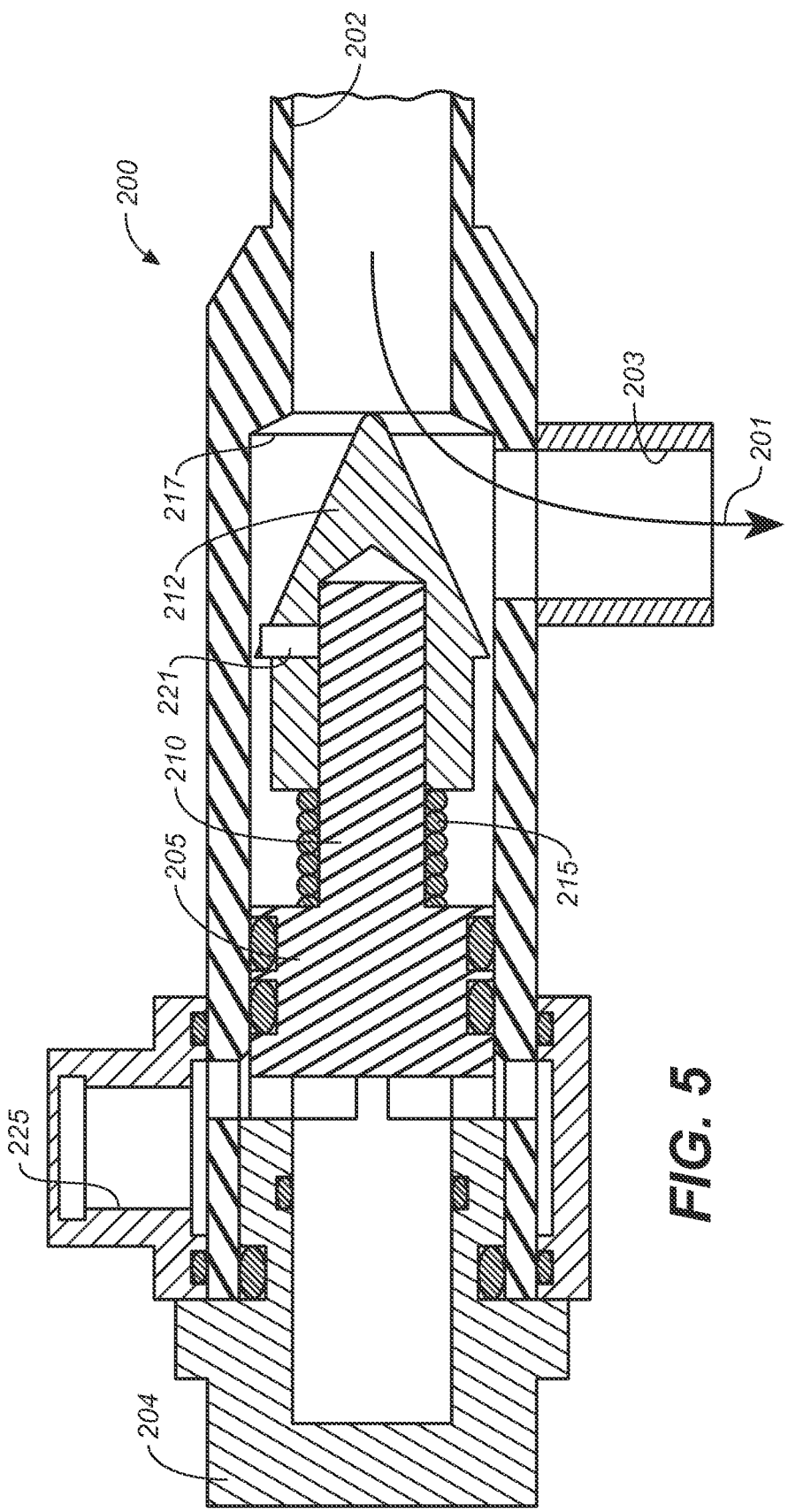
FIG. 5 is an enlarged section view showing the remotely operable valve in the open position, in accordance with an embodiment of the present invention.
Figure 6:
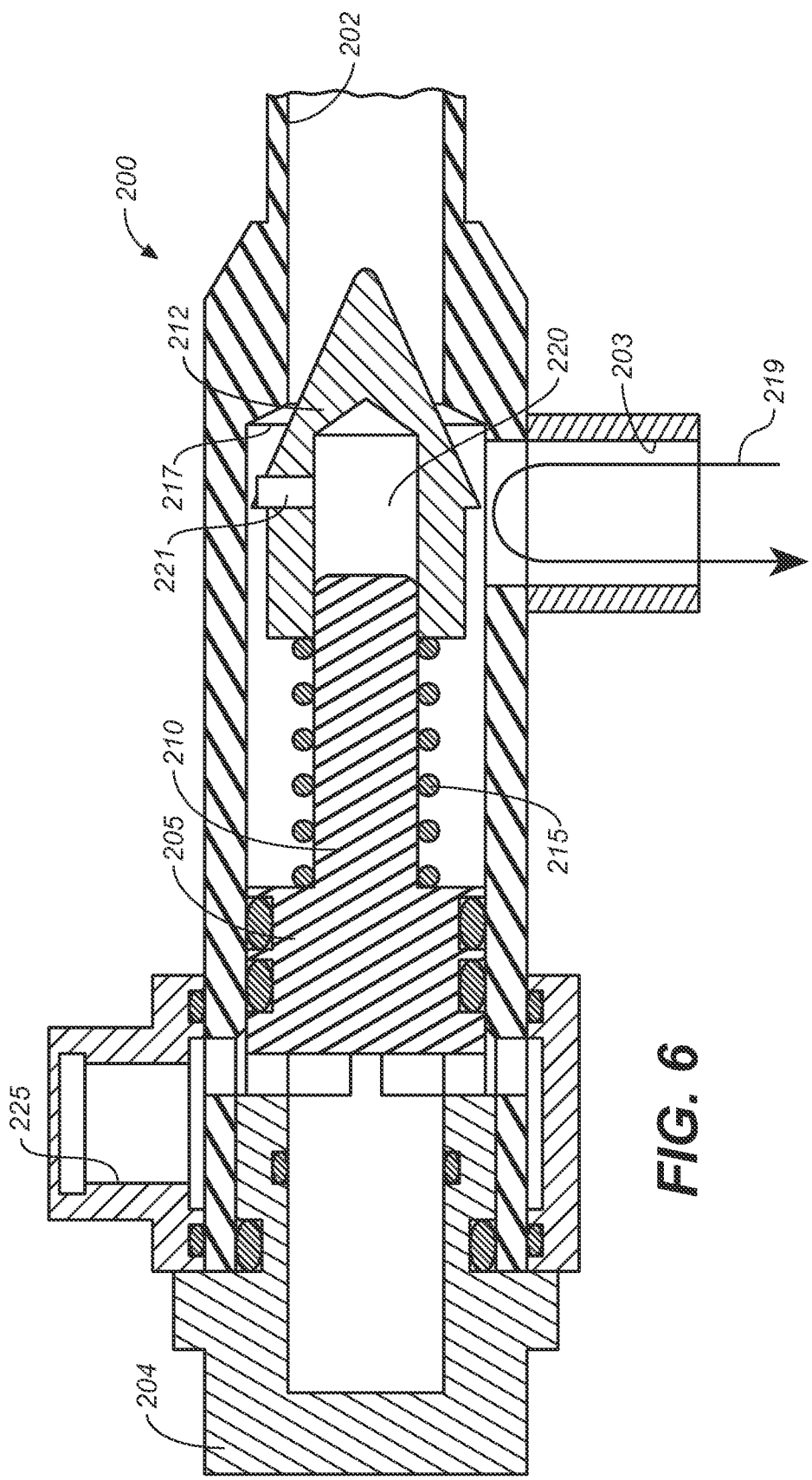
FIG. 6 is a section view showing the valve of FIG. 5 in a closed position, in accordance with an embodiment of the present invention.
Figure 7:
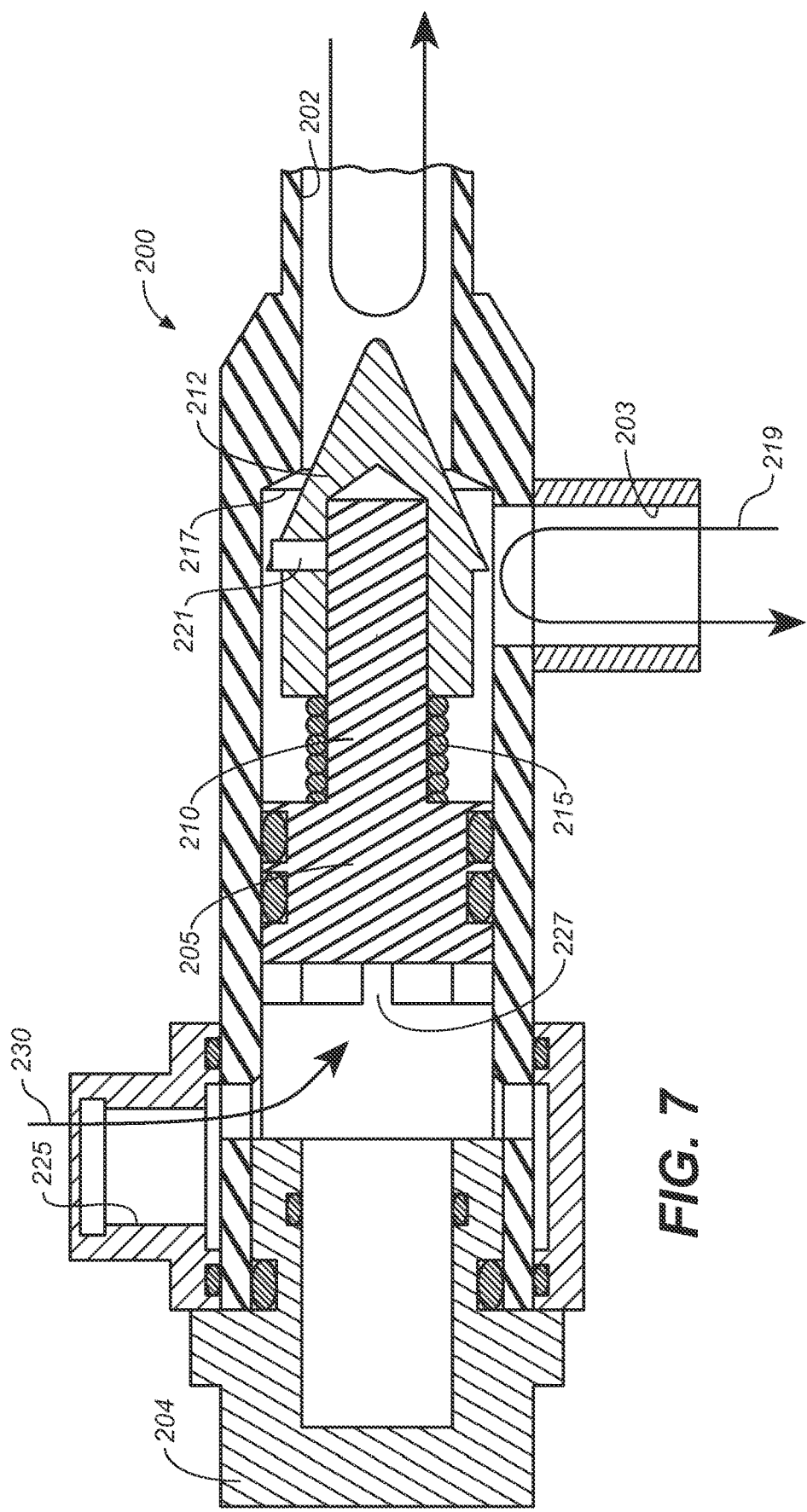
FIG. 7 is a section view showing the valve of FIG. 5 in a locked-out position, in accordance with an embodiment of the present invention.

FIGS. 5, 6 and 7 are enlarged views showing the remotely controllable valve 200 in various positions. In FIG. 5, the remotely controllable valve 200 is in a damping-open position (and a fluid path (denoted by 201 of FIG. 5) is obtained) thereby permitting operation in a compression stroke of electronically controlled damper link 14. The remotely controllable valve 200 includes a valve body 204 housing a movable piston 205 which is sealed within the body. Three fluid communication points are provided in the body including an inlet 202 and outlet 203 for fluid passing through the remotely controllable valve 200 as well as an inlet 225 for control fluid as will be described herein. Extending from a first end of the piston 205 is a shaft 210 having a cone-shaped member 212 (other shapes such as spherical or flat, with corresponding seats, will also work suitably well) disposed on an end thereof. The cone-shaped member 212 is telescopically mounted relative to, and movable on, the shaft 210 and is biased in an extended position (FIG. 6) due to a spring 215 coaxially mounted on the shaft 210 between the cone-shaped member 212 and the piston 205. Due to the spring 215 biasing, the cone-shaped member 212 normally seats itself against a seat 217 formed in an interior of the valve body 204. In the damping open position shown however, fluid flow through the damper link 14 has provided adequate force on the cone-shaped member 212 to urge it backwards, at least partially loading the spring 215 and creating fluid path 201 from the damper link 14 into a rebound area of the damper cylinder 141 as shown in FIG. 2A. The characteristics of the spring 215 are typically chosen to permit the remotely controllable valve 200 (e.g. cone-shaped member 212) to open at a predetermined bypass pressure, with a predetermined amount of control pressure applied to inlet 225, during a compression stroke of electronically controlled damper link 14. For a given spring 215, higher control pressure at inlet 225 will result in higher bypass pressure required to open the remotely controllable valve 200 and correspondingly higher damping resistance in electronically controlled damper link 14. In one embodiment of sway bar system 100, the remotely controllable valve 200 is open in both directions when the piston 205 is "topped out" against valve body 204. In another embodiment of sway bar system 100 however, when the piston 205 is abutted or "topped out" against valve body 204 the spring 215 and relative dimensions of the remotely controllable valve 200 still allow for the cone-shaped member 212 to engage the valve seat thereby closing the remotely controllable valve 200. In such an embodiment of sway bar system 100, backflow from the rebound portion 103 of the damper cylinder 141 to the compression portion 104 is always substantially closed and cracking pressure is determined by the pre-compression in the spring 215. In such embodiment, additional fluid pressure may be added to inlet 225 through port to increase the cracking pressure and thereby increase compression damping through electronically controlled damper link 14 over that value provided by the spring compression "topped out."

FIG. 6 shows remotely controllable valve 200 in a closed position (which it assumes during a rebound stroke of electronically controlled damper link 14). As shown, the cone-shaped member 212 is seated against seat 217 due to the force of the spring 215 and absent an opposite force from fluid entering the remotely controllable valve 200 from electronically controlled damper link 14. As cone-shaped member 212 telescopes out, a gap 220 is formed between the end of the shaft 210 and an interior of cone-shaped member 212. A vent 221 is provided to relieve any pressure formed in the gap 220. With the fluid path 201 closed, fluid communication is substantially shut off from the rebound portion 103 of electronically controlled damper link 14 into the valve body 204 (and hence through electronically controlled damper link 14 back to the compression portion 104 is closed) and its "dead-end" path is shown by arrow 219.

Inlet 225 is formed in the valve body 204 for operation of the remotely controllable valve 200. In one embodiment, inlet 225 may be pressurized to shift the remotely controllable valve 200 to a third or "locked-out" position. In FIG. 7, remotely controllable valve 200 is shown in the locked-out position, thereby preventing fluid flow through electronically controlled damper link 14 in either direction regardless of compression or rebound stroke. In the embodiment shown, inlet 225 provides a fluid path 230 to a piston surface 227 formed on an end of the piston 205, opposite the cone-shaped member 212. Specifically, activating pressure is introduced via inlet 225 to move the piston 205 and with it, cone-shaped member 212 toward seat 217. Sufficient activating pressure fully compresses the spring 215 (substantial stack out) and/or closes the gap 220 thereby closing the cone-shaped member 212 against the seat, sealing electronically controlled damper link 14 to both compression flow and rebound flow. In the embodiment shown, remotely controllable valve 200 can be shifted to the third, locked-out position from either the first, open position or the second, closed position. Note that, when in the "locked out" position, remotely controllable valve 200 as shown, will open to compression flow when the compression flow pressure acting over the surface area of the cone-shaped member 212 exceeds the inlet 225 pressure acting over the surface area of the piston 205. Such inlet 225 pressure may be selected to correspond therefore to a desired compression overpressure relief value or "blow off" value thereby allowing compression bypass under "extreme" conditions even when electronically controlled damper link 14 is "locked out".

In the embodiment illustrated, remotely controllable valve 200 is intended to be shifted to the locked-out position with control fluid acting upon piston 205. In one embodiment, the activating pressure via inlet 225 is adjusted so that remotely controllable valve 200 is closed to rebound fluid (with the cone-shaped member 212 in seat 217) but with the spring 215 not fully compressed or stacked out. In such a position, a high enough compression force (e.g. compression flow) will still open remotely controllable valve 200 and allow fluid to pass through remotely controllable valve 200 in a compression stroke. In one arrangement, the activating pressure, controlled remotely, may be adjusted between levels where the lock-out is not energized and levels where the lock-out is fully energized. The activating pressure may also be adjusted at intermediate levels to create more or less damping resistance through electronically controlled damper link 14. The activating pressure may be created by hydraulic or pneumatic input or any other suitable pressure source.

In one example of sway bar system 100, remotely controllable valve 200 is moved to a locked-out position and the electronically controlled damper link 14 is stiffened by remote control from a simple operator-actuated switch located in the passenger compartment of the vehicle. In one embodiment of sway bar system 100, fluid pressure for controlling (e.g. locking-out) remotely controllable valve 200 is provided by the vehicle's on-board source of pressurized hydraulic fluid created by, for example, the vehicle power steering system. In one embodiment, pneumatic pressure is used to control (e.g. close) remotely controllable valve 200 where the pneumatic pressure is generated by an on-board compressor and accumulator system and conducted to remotely controllable valve 200 via a fluid conduit. In one embodiment of sway bar system 100, a linear electric motor (e.g. solenoid), or other suitable electric actuator, is used, in lieu of the aforementioned inlet 225 pressure, to move "piston 205" axially within valve body 204. A shaft of the electric actuator (not shown) may be fixed to the piston 205 such that axial movement of the shaft causes axial movement of piston 205 which in turn causes movement of cone-shaped member 212 (and compression of spring 215 as appropriate). In one embodiment, the electric actuator is configured to "push" piston 205 towards a closed position and to "pull" piston 205 away from the closed position depending on the direction of the current switched through the actuator.

As in other embodiments, remotely controllable valve 200 may be solenoid operated or hydraulically operated or pneumatically operated or operated by any other suitable motive mechanism. Remotely controllable valve 200 may be operated remotely by a switch 415 or potentiometer located in the cockpit of a vehicle or attached to appropriate operational parts of a vehicle for timely activation (e.g. brake pedal) or may be operated in response to input from a microprocessor (e.g. calculating desired settings based on vehicle acceleration sensor data) or any suitable combination of activation means. In a like manner, a controller for the adjustable pressure source (or for both the source and the valve) may be cockpit mounted and may be manually adjustable or microprocessor controlled or both or selectively either.

In one embodiment of sway bar system 100, a pressure intensifier damper arrangement is located within the fluid path such that the solenoid-controlled valve controls flow through that auxiliary damper which is then additive with the damper mechanism of the damping piston. In one embodiment of sway bar system 100, the damper mechanism of the damping piston comprises a pressure intensifier. In one embodiment one or both of the dampers comprise standard shim type dampers. In one embodiment one or both of the dampers include an adjustable needle for low speed bleed. In one embodiment, a blow off (e.g. checking poppet type or shim) is included in one of the flow paths or in a third parallel flow path.

Figure 8:
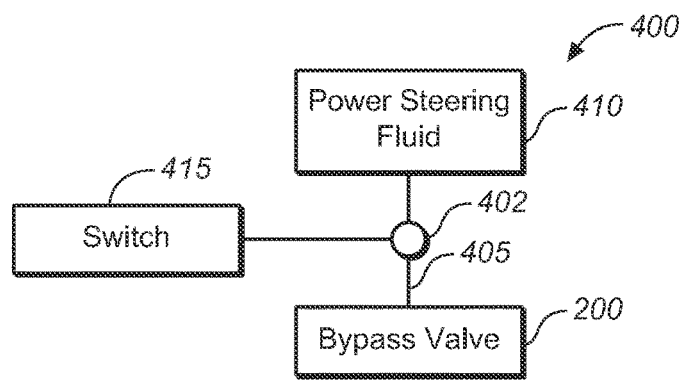
FIG. 8 is a schematic diagram showing a control arrangement for a remotely operated valve, in accordance with an embodiment of the present invention.

FIG. 8 is a schematic diagram illustrating a control arrangement 400 used to provide remote control of a remotely controllable valve 200 using a vehicle's power steering fluid 410 (although any suitable fluid pressure source may be substituted for power steering fluid 410 as could be an electrical current source in the case of a remotely controllable valve 200). As illustrated, a fluid pathway 405 having a switch-operated valve (and/or pressure regulator) 402 therein runs from power steering fluid 410 (or an electrical current) that is kept pressurized by, in one embodiment, a power steering pump (not shown) to a remotely controllable valve 200 that is operable, for example, by a user selectable dash board switch 415. The switch-operated valve 402 permits fluid to travel to remotely controllable valve 200, thereby urging it to a closed position. When switch 415 is in the "off" position, working pressure within electronically controlled damper link 14, and/or a biasing member such as a spring or annular atmospheric chamber (not shown), returns electronically controlled damper link 14 to its normally-open position (with or without residual spring compression as designed). In another embodiment, a signal line runs from switch 415 to a solenoid along an electrically conductive line. Thereafter, the solenoid converts electrical energy into mechanical movement (identified by item 405) and shifts a plunger of remotely controllable valve 200, thereby opening or closing the valve or causing the plunger to assume some predetermined position in-between. Hydraulically actuated valving for use with additional components is shown and described in U.S. Pat. No. 6,073,536 and that patent is incorporated by reference herein in its entirety.

While the example of FIG. 8 uses fluid power for operating remotely controllable valve 200, a variety of means are available for remotely controlling a remotely controllable valve 200. For instance, a source of electrical power from a 12 volt battery could be used to operate a solenoid member, thereby shifting a piston 205 in remotely controllable valve 200 between open and closed positions. Remotely controllable valve 200 or solenoid operating signal can be either via a physical conductor or an RF signal (or other wireless such as Bluetooth, WiFi, ANT) from a transmitter operated by the switch 415 to a receiver operable on the remotely controllable valve 200 (which would derive power from the vehicle power system such as 12 volt).

Remotely controllable valve 200 like the one described above is particularly useful with an on/off road vehicle. Operating a vehicle with very compliant, conventional sway bar on a smooth road at higher speeds can be problematic due to the springiness/sponginess of the suspension and corresponding vehicle handling problems associated with that (e.g. turning roll, braking pitch). Such compliance can cause reduced handling characteristics and even loss of control. Such control issues can be pronounced when cornering at high speed as a vehicle with a conventional compliant sway bar may tend to roll excessively. With remotely operated electronically controlled damper link 14 dampening and "lock out" described herein, dampening characteristics of electronically controlled damper link 14 can be adjusted, and as such, sway bar system 100 can be completely changed from a compliantly dampened "springy" arrangement to a highly dampened and "stiffer" (or fully locked out) system ideal for higher speeds on a smooth road.

In one embodiment, where compression flow is completely blocked, closure of electronically controlled damper link 14 results in substantial "lock out" of the sway bar system 100 (sway bar system 100 is rendered essentially rigid except for the movement of fluid through shimmed valve). In another embodiment where some compression flow is allowed, closure of electronically controlled damper link 14 (e.g., by closure of remotely controllable valve 200) results in a stiffer but still functional sway bar system 100.

In addition to, or in lieu of, the simple, switch operated remote arrangement of FIG. 8; the remotely controllable valve 200 can be operated automatically based upon one or more driving conditions.

Figure 9:
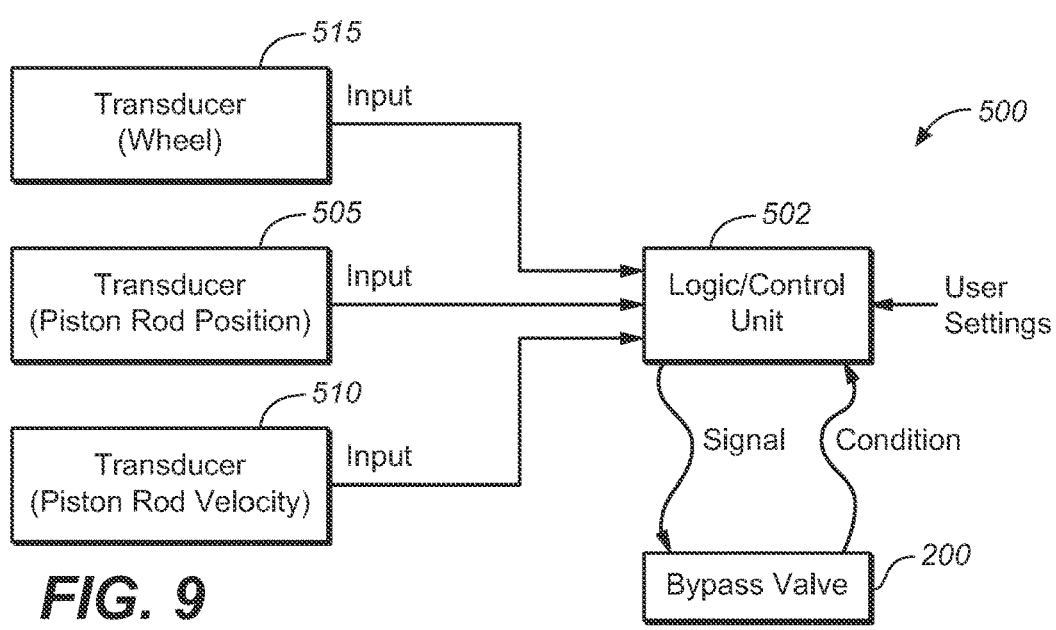
FIG. 9 is a schematic diagram showing another control arrangement for a remotely operated valve, in accordance with an embodiment of the present invention.
Figure 10:
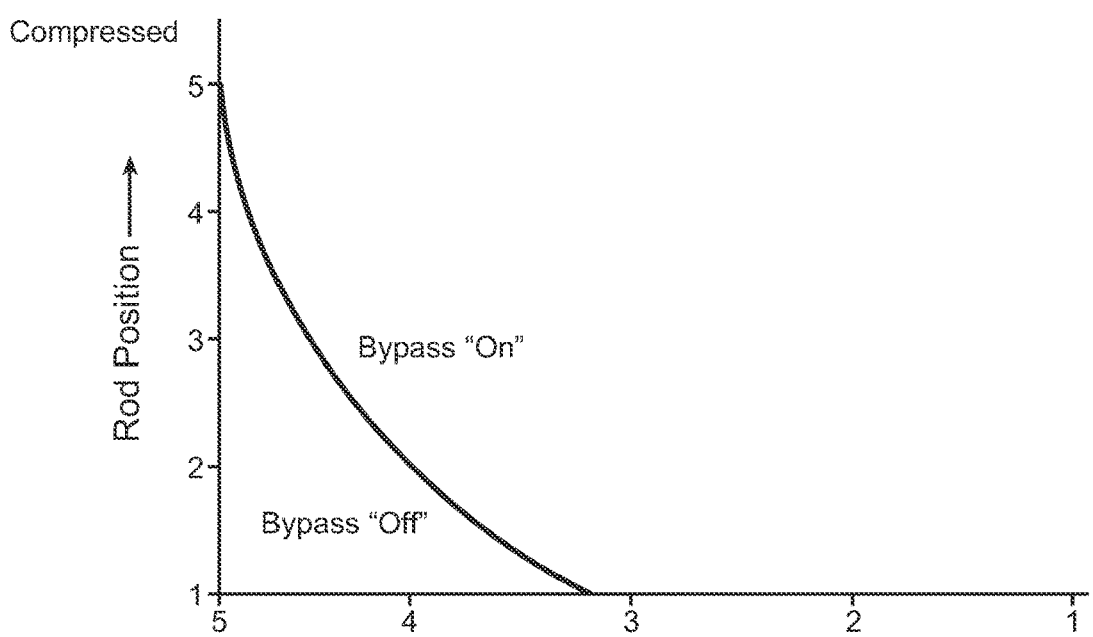
FIG. 10 is a graph showing some operational characteristics of the arrangement of FIG. 7, in accordance with an embodiment of the present invention.

FIG. 9 illustrates, for example, a system including three variables: shaft speed, shaft position and vehicle speed. Any or all of the variables shown may be considered by processor 502 in controlling the solenoid in the remotely controllable valve 200. Any other suitable vehicle operation variable may be used in addition to or in lieu of the variables 515, 505, 510 such as for example, a vehicle mounted accelerometer (or tilt/inclinometer) data or any other suitable vehicle or component performance data. In one embodiment the position of piston 105 within damper cylinder 141 is determined using an accelerometer to sense modal resonance of damper cylinder 141. Such resonance will change depending on the position of the piston 105 and an on-board processor (computer) is calibrated to correlate resonance with axial position. In one embodiment, a suitable proximity sensor or linear coil transducer or other electro-magnetic transducer is incorporated in the damper cylinder 141 to provide a sensor to monitor the position and/or speed of the piston 105 (and suitable magnetic tag) with respect to the damper cylinder 141. In one embodiment, the magnetic transducer includes a waveguide and a magnet, such as a doughnut (toroidal) magnet that is joined to the cylinder and oriented such that the magnetic field generated by the magnet passes through shaft 24 and the waveguide. Electric pulses are applied to the waveguide from a pulse generator that provides a stream of electric pulses, each of which is also provided to a signal processing circuit for timing purposes. When the electric pulse is applied to the waveguide a magnetic field is formed surrounding the waveguide. Interaction of this field with the magnetic field from the magnet causes a torsional strain wave pulse to be launched in the waveguide in both directions away from the magnet. A coil assembly and sensing tape is joined to the waveguide. The strain wave causes a dynamic effect in the permeability of the sensing tape which is biased with a permanent magnetic field by the magnet. The dynamic effect in the magnetic field of the coil assembly due to the strain wave pulse, results in an output signal from the coil assembly that is provided to the signal processing circuit along signal lines. By comparing the time of application of a particular electric pulse and a time of return of a sonic torsional strain wave pulse back along the waveguide, the signal processing circuit can calculate a distance of the magnet from the coil assembly or the relative velocity between the waveguide and the magnet. The signal processing circuit provides an output signal, either digital, or analogue, proportional to the calculated distance and/or velocity. A transducer-operated arrangement for measuring shaft speed and velocity is described in U.S. Pat. No. 5,952,823 and that patent is incorporated by reference herein in its entirety.

While a transducer assembly located at electronically controlled damper link 14 measures shaft speed and location, a separate wheel speed transducer for sensing the rotational speed of a wheel about an axle includes housing fixed to the axle and containing therein, for example, two permanent magnets. In one embodiment the magnets are arranged such that an elongated pole piece commonly abuts first surfaces of each of the magnets, such surfaces being of like polarity. Two inductive coils having flux-conductive cores axially passing therethrough abut each of the magnets on second surfaces thereof, the second surfaces of the magnets again being of like polarity with respect to each other and of opposite polarity with respect to the first surfaces. Wheel speed transducers are described in U.S. Pat. No. 3,986,118 which is incorporated herein by reference in its entirety.

While the examples illustrated relate to manual operation and automated operation based upon specific parameters, remotely controllable valve 200 or the remote operation of a pressure source can be used in a variety of ways with many different driving and road variables. In one example, remotely controllable valve 200 is controlled based upon vehicle speed in conjunction with the angular location of the vehicle's steering wheel. In this manner, by sensing the steering wheel turn severity (angle of rotation), additional dampening can be applied to stiffen electronically controlled damper link 14 thereby stiffening sway bar system 100 (suitable, for example, to mitigate cornering roll) in the event of a sharp turn at a relatively high speed. In another example, a transducer, such as an accelerometer, measures other aspects of the vehicle's suspension system, like axle force and/or moments applied to various parts of the vehicle, like steering tie rods, and directs change to electronically controlled damper link 14 and thus the compliance or stiffness of sway bar system 100 in response thereto.

It should be noted that any of the features disclosed herein are useful alone or in any suitable combination. While the foregoing is directed to embodiments of the present invention, other and further embodiments of the invention is implemented without departing from the scope of the invention and the scope thereof is determined by the Claims that follow.

What is claimed is:

1. A sway bar system comprising:
    a sway bar having a first end and a second end;
    a first electronically controlled damper link coupled to said first end of said sway bar and said first electronically controlled damper link configured to be coupled to a first location of a vehicle, said first electronically controlled damper link comprising:
        a damper having a remotely controllable valve for adjusting damping characteristics of said damper, said remotely controllable valve controllable based upon received sensor input, wherein said damper further comprises:
            an internal floating piston disposed on a rebound side of said damper; and
            a check valve, wherein when said check valve is in an open position, said internal floating piston and said check valve reduce a damping force of said first electronically controlled damper link to mitigate an occurrence of cavitation; and
    a second electronically controlled damper link coupled to said second end of said sway bar and said second electronically controlled damper link configured to be coupled to a second location of said vehicle.

2. The sway bar system of claim 1, wherein said second electronically controlled damper link further comprises:
    said second electronically controlled damper link coupled to said second end of said sway bar, said second electronically controlled damper link configured to be coupled to a second location of said vehicle, said second electronically controlled damper link comprising:
        a second damper having a second remotely controllable valve for adjusting damping characteristics of said second damper, said second remotely controllable valve controllable based upon received sensor input.

3. The sway bar system of claim 2, wherein said second damper is selected from the group consisting of: a non-twin tube damper and a twin tube damper.

4. The sway bar system of claim 1, wherein said damper is selected from the group consisting of: a non-twin tube damper and a twin tube damper.

5. The sway bar system of claim 1, wherein said damper further comprises:
    a damper cylinder having a diameter and a volume;
    a shaft having a diameter, said shaft configured to move into and out of said damper cylinder; and
    a gas chamber fluidly coupled with said damper cylinder.

6. The sway bar system of claim 5, wherein a ratio of said damper cylinder diameter to said shaft diameter is adjusted to reduce reaction forces on said shaft.

7. The sway bar system of claim 5, wherein a ratio of said damper cylinder volume to a flow area of said remotely controllable valve is adjusted to reduce an initial gas pressure in said gas chamber and reduce a damping force on said first electronically controlled damper link when said first electronically controlled damper link is in a decoupled setting.

8. The sway bar system of claim 5, wherein said damper further comprises:
    a second damper cylinder having a diameter and a volume, said diameter of said second damper cylinder smaller than said diameter of said damper cylinder, said second damper cylinder disposed concentrically within said damper cylinder.

9. The sway bar system of claim 8, wherein said damper further comprises:
    a body cap; and
    a seal head, said body cap and said seal head configured to couple with both said damper cylinder and said second damper cylinder.

10. The sway bar system of claim 1, wherein said remotely controllable valve further comprises:
a valve body;
a movable piston disposed within said valve body, said movable piston further comprising:
an end portion;
a shaft extending from said end portion;
a member movably coupled to said shaft; and
a biasing feature coupled with said member;
an inlet configured to allow fluid to pass into said remotely controllable valve;
an outlet configured to allow fluid to pass out of said remotely controllable valve, wherein said biasing feature forces said member against said inlet, wherein said member is configured to be moved away from said inlet and allow said fluid to pass into said remotely controllable valve provided said fluid provides adequate force against said member; and
a control inlet configured to fluid adjust a position of said movable piston within said valve body.

11. The sway bar system of claim 10, wherein said biasing feature is configured to force said member against said inlet such that said member is moved away from said inlet and allows said fluid to pass into said remotely controllable valve at a predetermined bypass pressure.

12. The sway bar system of claim 11, wherein an increase in said bypass pressure correspondingly increases damping resistance of said first electronically controlled damper link.

13. The sway bar system of claim 10, wherein a cracking pressure of said remotely controllable valve is configured to be increased by increasing a fluid pressure at said control inlet.

14. The sway bar system of claim 13, wherein an increase in said cracking pressure correspondingly increases damping resistance of said first electronically controlled damper link.

15. The sway bar system of claim 10, wherein said member has a shape selected from the group consisting of: conical, spherical and flat.

16. The sway bar system of claim 10, wherein said biasing feature is a spring coaxially mounted on said shaft.

17. The sway bar system of claim 10, wherein said remotely controllable valve controls fluid flow between a compression side and a rebound side of said damper.

18. The sway bar system of claim 10, wherein remotely controllable valve permits operation of a compression stroke for said first electronically controlled damper link when said remotely controllable valve is in an open position wherein said member does not prevent fluid from flowing through said inlet.

19. The sway bar system of claim 10, wherein remotely controllable valve permits operation of a rebound stroke for said first electronically controlled damper link when said remotely controllable valve is in a closed position wherein said member prevents fluid from flowing through said inlet.

\* \* \* \* \*